United States Patent [19]
David et al.

[11] Patent Number: 6,125,948
[45] Date of Patent: Oct. 3, 2000

[54] SOIL SAMPLING DEVICE WITH FRANGIBLE SECTION

[75] Inventors: Ramon R. David, Holland; Saeid Yazdani, Byron Center, both of Mich.

[73] Assignee: Soil Core, Inc., Holland, Mich.

[21] Appl. No.: 09/186,925

[22] Filed: Nov. 6, 1998

Related U.S. Application Data

[63] Continuation-in-part of application No. 09/135,266, Aug. 17, 1998.

[51] Int. Cl.[7] .................................................. E21B 49/00
[52] U.S. Cl. .............................. 175/58; 175/20; 175/226; 73/864.44; 73/864.45
[58] Field of Search ................................ 175/20, 58, 226, 175/244, 249, 320; 73/864.44, 864.45, 864.91; 413/12, 15

[56] References Cited

U.S. PATENT DOCUMENTS

| | | | |
|---|---|---|---|
| 1,737,718 | 12/1929 | Hausmann | 220/266 |
| 1,847,136 | 3/1932 | Rauberstrauch | 175/87 |
| 2,288,210 | 6/1942 | Schlumberger | 255/1 |
| 2,664,269 | 12/1953 | Knight et al. | 255/1 |
| 3,326,049 | 6/1967 | Eley | 73/429 |
| 3,412,814 | 11/1968 | Rosfelder | 175/6 |
| 3,497,018 | 2/1970 | Shultz et al. | 175/6 |
| 3,970,156 | 7/1976 | Niskin | 175/58 X |
| 4,549,612 | 10/1985 | Cushing | 175/20 |
| 4,729,437 | 3/1988 | Zapico | 175/20 |
| 4,819,735 | 4/1989 | Puckett | 172/22 |
| 4,989,678 | 2/1991 | Thompson | 175/20 |
| 5,245,878 | 9/1993 | Underwood | 73/864.44 |
| 5,343,771 | 9/1994 | Turriff et al. | 73/864.44 |
| 5,505,098 | 4/1996 | Turriff et al. | 73/864.44 |
| 5,517,868 | 5/1996 | Turiff et al. | 175/58 X |
| 5,522,271 | 6/1996 | Turriff et al. | 73/864.44 |
| 5,706,904 | 1/1998 | Turriff et al. | 175/28 |
| 5,937,953 | 8/1999 | Melberg et al. | 175/20 |

*Primary Examiner*—David Bagnell
*Assistant Examiner*—Jong-Suk Lee
*Attorney, Agent, or Firm*—Van Dyke, Gardner, Linn & Burkhart

[57] ABSTRACT

A soil sampling device for collecting samples of soil provides a single use unit with an integrally molded plunger. The soil sampling device includes a cylindrical body having a first chamber and a second chamber, with each chamber comprising a cylindrical wall having a longitudinal axis and an end wall. Optionally, the sampling device may include additional chambers depending on the application. An open end of each chamber defines a mouth which is adapted for inserting into soil. A piston may be positioned within each chamber, and the end walls include a projecting member extending outwardly therefrom which defines a plunger. The end wall includes a reduced cross-section around the projecting member and is adapted to break when a force is applied to the projecting member to thereby permit the plunger enter into the body and thereby push the piston along the longitudinal axis to expel a sample of soil collected in the body. Preferably, the piston is frictionally held in the body, for example by frictionally engaging an inner surface of the cylindrical wall. Optionally, the piston includes at least one seal for frictionally engaging the inner surface of the cylindrical wall.

47 Claims, 8 Drawing Sheets

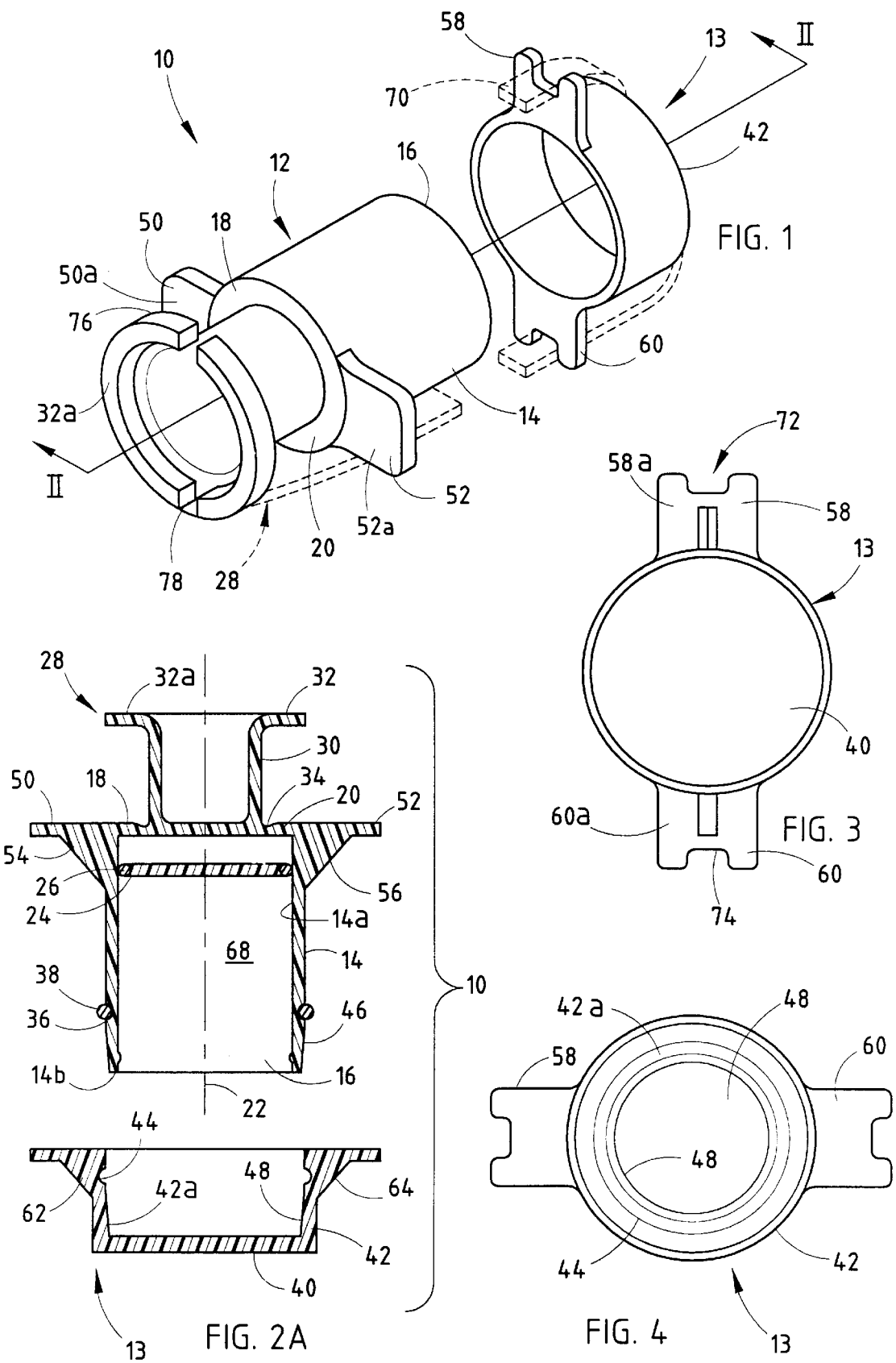

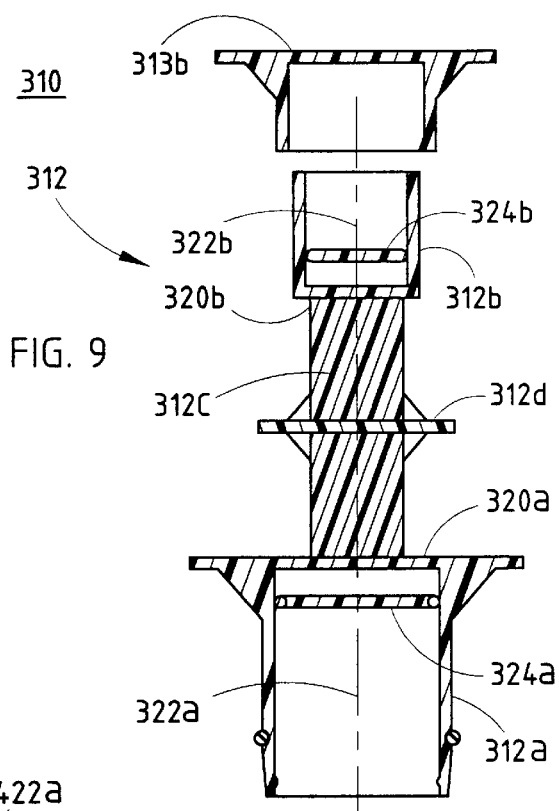
FIG. 9
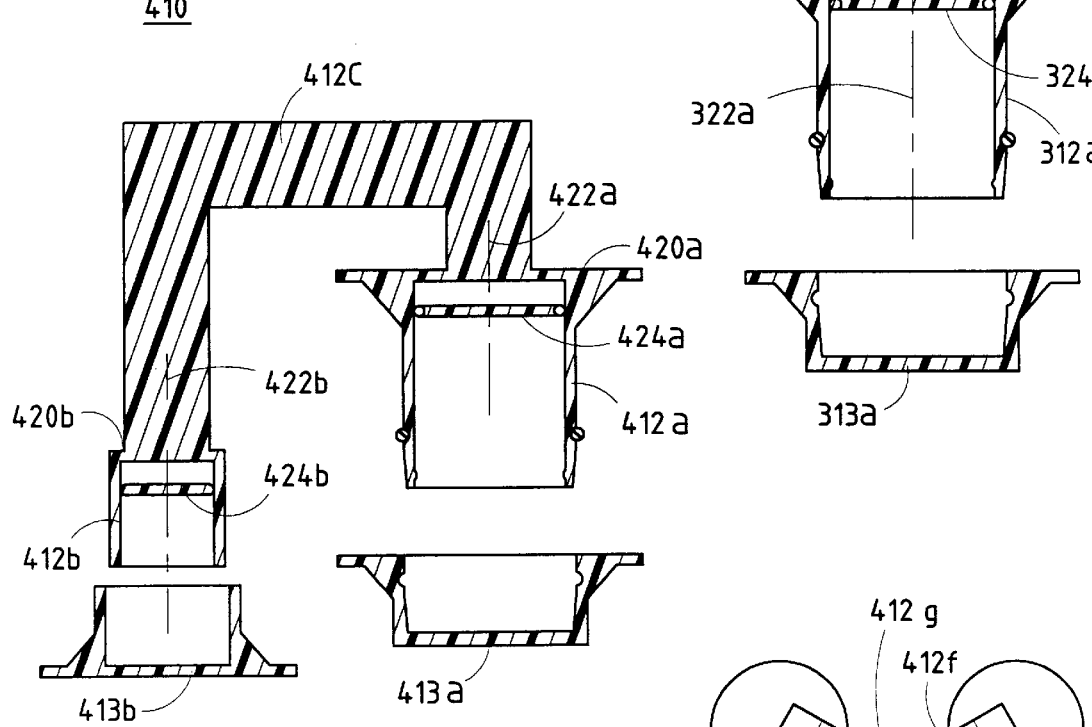
FIG. 10A
FIG. 10C

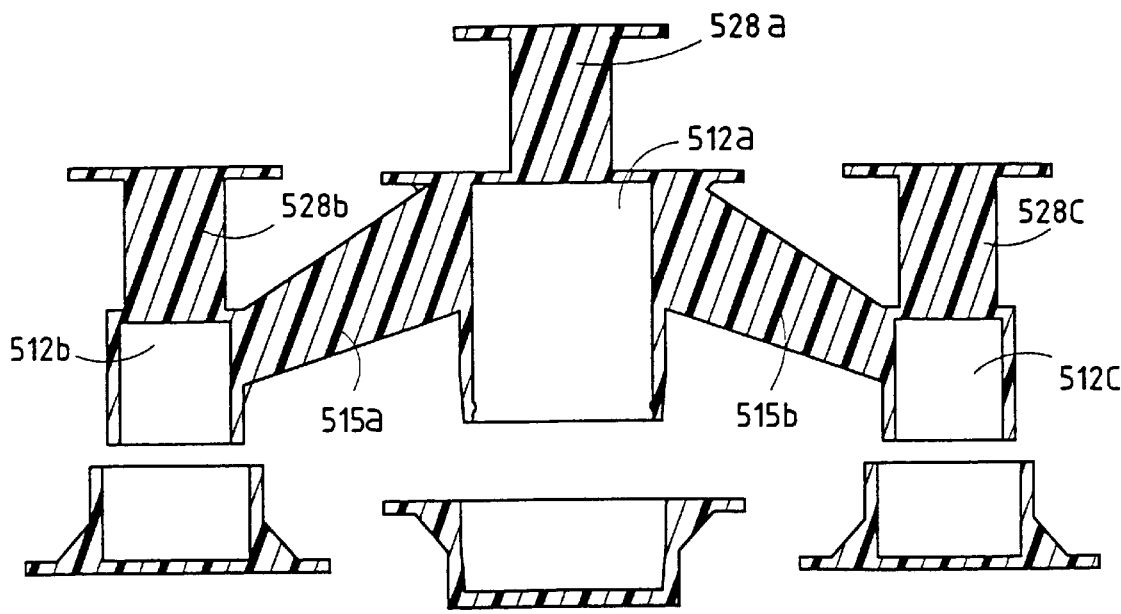
FIG. 11B
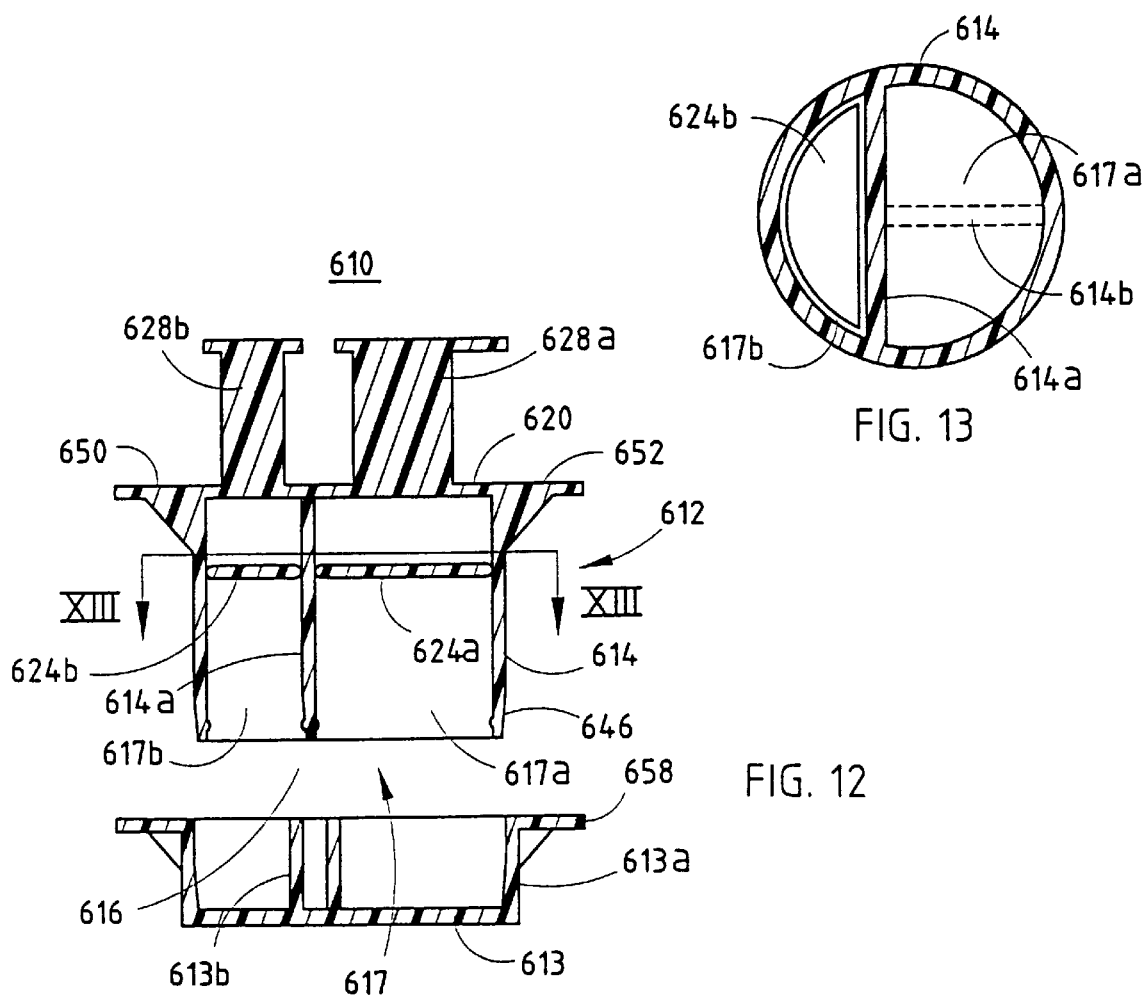
FIG. 13
FIG. 12

SOIL SAMPLING DEVICE WITH FRANGIBLE SECTION

RELATED APPLICATION

This is a continuation-in-part application of patent application Ser. No. 09/135,266, entitled SOIL SAMPLING DEVICE, filed on Aug. 17, 1998, which is hereby incorporated herein by reference.

TECHNICAL FIELD AND BACKGROUND OF THE INVENTION

The present invention relates to a soil sampling device and, more particularly, to a self contained soil sampling device for obtaining soil samples for soil testing.

Soil sampling devices are used to obtain a sample of soil for analyzing the soil content including, for example, volatile organic compounds (VOCs) which may have permeated the soil. Typically, soil sampling devices include a barrel which includes an open end for inserting into the soil and a plunger which is adapted to extend through the barrel to expel the collected soil sample from the barrel for subsequent testing. Often, the soil sampling devices include a removable cover which is placed over the open end of the barrel after the soil sample has been taken so that the soil sampling device can be transported to a laboratory setting, including for example testing facilities which may be located at the soil sampling site, where the cap is then removed and the soil is expelled from the barrel by the plunger.

For example, in U.S. Pat. No. 5,706,904 to Turriff et al., a reusable soil sampling device is disclosed which includes a barrel and a plunger assembly. The plunger assembly includes a shaft which extends to the end wall of the barrel and a piston mounted to the distal end of the shaft and a pair of outwardly extending arms mounted to the medial portion of the shaft. Initially, the plunger assembly is fully extended into the barrel such that the plunger is generally positioned at the mouth of the barrel. When taking a soil sample, however, the plunger is pulled through the barrel, somewhat like a syringe, during which time the barrel is filled with soil. The Turriff piston includes a pair of seals which engage the inner surface of the barrel to minimize the loss of the VOCs in the soil during the filling of the barrel. Once the barrel is completely filled with the soil sample, the arms of the piston assembly are rotated and seated in a holding structure provided on the end wall of the barrel. In this manner, the piston assembly is in a fixed, fully retracted position in the barrel. In order to expel the soil sample from the barrel, the arms are then rotated back to a release position so that the plunger can then be again extended into the barrel to thereby expel the soil sample from the barrel with the piston. However, it has been found that the piston assembly is hard to manipulate, and that over time, the space between the shaft of the piston and the end wall of the barrel may become clogged with soil and, thus, prevent the piston from properly operating.

In U.S. Pat. No. 5,343,771, another reusable soil sampling device is disclosed which includes a barrel and a piston assembly which is slidably mounted in the barrel through an end wall of the barrel. The piston assembly includes a shaft and a piston on one end of the shaft and a handle on the opposed end of the shaft. The piston assembly is biased in a retracted position in the barrel by a spring which is positioned between the handle and a handle of the barrel. The soil sampling device further includes a cap which is mounted to the open end of the barrel after the soil sample has been taken. Other such arrangements can be found in U.S. Pat. No. 3,326,049 to Eley. In the Eley device, the plunger assembly includes a scale on the shaft of the plunger assembly in order to read the displaced volume of the sample when soil is expelled from the barrel. The Eley sampling device permits several samples to be taken from a single core sample.

In U.S. Pat. No. 5,522,271 to Turriff et al., a soil sampling device is disclosed which includes a barrel and a plug, which is integrally molded with the barrel. The plug is positioned inside the barrel and is spaced from the mouth portion. The plug includes a frangible section which is integrally molded with the barrel. In order to obtain a soil sample, however, the frangible section must be supported by a support member which is inserted into the second open end of the barrel and extended into the barrel to make direct contact with the plug. After a soil sample has been taken, a cap is placed over the open end of the barrel to retain the soil sample therein. In order to expel the soil sample for later testing, the support member is removed from the barrel and a second device (55) is inserted into the barrel to apply a force to the plug to thereby break the frangible section in order to expel the soil sample. Thus, the Turriff'271 soil sampling device requires four components: The barrel; the cap; the support member; and the expulsion device (55). As a result, the Turriff'271 device is relatively complicated to use and ultimately, as a result of the several component parts, is more costly than most conventional sampling devices.

The process of collecting soil samples typically includes collecting at least two samples, one for analyzing the soil content and a second sample for determining the dry weight of the soil being analyzed. Additionally, there are soil sampling guidelines and regulations which require a different sample size depending on the contents of various compounds within the soil. For example, the Environmental Protection Agency (EPA) has set forth regulations regarding the collection of soil or oily waste samples that are to be analyzed for their content of VOCs, which require that either a 25 g sample or a 5 g sample be collected depending on the levels of analytes present at the sampling site. Therefore, if an area to be sampled has no previous analytical history, both samples must be taken, in addition to a dry weight sample, to avoid a second trip to the site to collect the appropriate sample once the level of analytes is known. Even if the level of analytes is known prior to sampling the soil, a second sample is still required for determining the dry weight of the soil. Because the sampling devices proposed and discussed above include only a single barrel and plunger assembly or the like, multiple sampling devices are required when two or more separate samples must be collected. Furthermore, multiple sampling devices or jars are often required even when only a single sample is required for analytical purposes, as it is often necessary to collect a second sample for the dry weight analysis.

Consequently, there is a need for a simple single use soil sampling device which maintains the integrity of the VOCs in the soil sample, and yet provides the ease of sampling and expulsion of the collected soil sample with fewer steps and fewer components than heretofore known. Furthermore, the single use soil sampling device must accommodate multiple soil sample collection procedures by providing a sampling device having two or more chambers, thereby being capable of collecting two or more separate samples.

SUMMARY OF THE INVENTION

Accordingly, the present invention provides a new and unique soil sampling device, which is especially suitable for collecting multiple samples of soil for measuring the VOCs in the soil sample. The soil sampling device includes an improved piston assembly which is easy to use and requires fewer component parts.

According to one aspect of the invention, a soil sampling device includes a body and a piston positioned in the body. The body comprises a cylindrical wall having a longitudinal axis and an end wall, with the cylindrical wall extending between first and second ends of the body. The end wall is positioned at the first end of the body, and the second end of the body defines a mouth, which is adapted for inserting into the soil. The end wall includes a projecting member which extends outwardly from the body and which defines a plunger. The end wall includes a reduced cross section around the projecting member and is adapted to break when a force is apply to the projecting member to permit the plunger to enter into the body and, thereby, push the piston along the longitudinal axis of the body to expel a sample of soil collected in the body.

In preferred aspects of the invention, the piston is frictionally held in the body. For example, the piston may frictionally engage in an inner surface of the cylindrical wall. In a further aspect, the piston may include at least one seal, for frictionally engaging the inner surface of the cylindrical wall of the soil sampling body.

In yet other aspects, the reduced cross-section of the end wall is positioned radially inward of the cylindrical wall of the body. Furthermore, the reduced cross-section of the end wall preferably comprises an annular groove on the outer surface of the end wall which extends around the projecting member.

In other aspects of the invention, a method of sampling a soil includes providing a soil sampling device. The soil sampling device includes a body with first and second ends. The body of the soil sampling device includes a cylindrical wall and an end wall, with the cylindrical wall extending between the first and second ends of the body, and the end wall being positioned at the first end of the body. The second end of the body defines a mouth which is adapted for inserting into soil. The soil sampling device further includes a piston which is positioned in the body and a projecting member which extends outwardly from the end wall of the body. The projecting member defines a plunger. The end wall of the body includes an annular frangible section at an innerface between the plunger and the end wall. The mouth of the soil sampling device is inserted into the soil and subsequently removed to thereby collect a sample of soil. In order to eject the soil sample from the body of the soil sampling device, a force is applied to the projecting member to thereby break the frangible section of the end wall. The projecting member is then pushed into the body of the soil sampling device after breaking the frangible section to thereby expel the piston and the sample of the soil collected from the body of the soil sampling device.

In further aspects, the piston is retained in the body of the soil sampling device after the soil sample has been expelled from the body. In addition, the mouth of the body of the soil sampling device preferably is covered after removing the soil sampling device from the soil to retain integrity of the collected sample of soil.

According to another aspect of the invention, a soil sampling device includes a body, which further includes a plurality of interconnected chambers. Each of the chambers of the body further includes a mouth for inserting into the soil to collect the samples of soil and an end wall opposite the mouth. At least one plunger member is interconnected with at least one frangible section on at least one of the end walls, such that when a pressure is applied to the plunger member, the frangible section breaks and the plunger member provides a plunger for at least one of the chambers to expel soil contained therein.

In one form, a first chamber and a second chamber may be interconnected at the end wall of the first chamber, where at least a portion of the first end wall forms an end wall for the second chamber. The end wall of the first chamber includes a frangible section, such that when a pressure is applied to the second chamber to compress the end wall of the first chamber, the frangible section will break as the second chamber provides a plunger for the first chamber to expel the soil sample contained therein.

In another form, the first and second portions may be interconnected by a single plunger member, which is connected to an end wall of the first chamber and further connected to an end wall of the second chamber, such that the member may function as a plunger for at least one of the first and second chambers. The plunger member may extend co-axially between the first and second chambers of the sampling device, or alternately may be formed such that the first and second chambers of the sampling device are positioned substantially side by side one another. The sampling device may further include one or more additional chambers, with an end wall of each chamber being interconnected with the end walls of the other chambers by a plunger member having a plurality of arms equal to the number of chambers of the sampling device.

In yet another form, the plurality of chambers of the body of the soil sampling device may be interconnected by at least one connecting member between their respective side walls. The end walls may include a reduced cross-section around their respective plunger members and are adapted to break when a force is applied to the plunger member to permit the plunger member to enter into the respective chamber to expel the soil contained therein. In another form, additional chambers may be included that are likewise interconnected by the at least one connecting member.

In another aspect, the plurality of chambers may be included within a single cylindrical body, such that the cylindrical wall of the body is compartmentalized to form a first and second chamber of the soil sampling device. Again, at least one plunger member may be included at an end wall of the soil sampling device to provide a plunger to expel soil that is contained within at least one of the first and second portions. In another form, the single body may be compartmentalized into three or more chambers.

In other aspects, a soil sampling device further includes at least one cap, which closes at least one of the first and second chambers of the body after a soil sample has been taken. The cap is preferably releasably mounted to the body, for example, the cap may be frictionally held on the body. In one form, the cap includes a tapered inner surface, which frictionally engages an end portion of the cylindrical wall to thereby frictionally hold the cap on the body. In other forms, the body includes a seal, which seal frictionally holds the cap on the body. For example, the seal may comprise a strip seal or an O-ring seal. In preferred form, either the body or the cap includes a groove for holding the seal on the soil sampling device. In further forms, a second groove may be provided on the other of the body or the cap to receive the seal.

As will be understood, the soil sampling device of the present invention provides numerous advantages over prior known soil sampling devices. The soil sampling device provides a single use device which consists of two parts, the soil sampling device body and piston and the cap. The soil sampling device is simple to use and overcomes the handling problems of prior known soil sampling devices since the plunger assembly is integrally molded with the end wall of the soil sampling device body and is not actuated until impacted. Furthermore, the piston which ejects the soil sample from the body of the soil sampling device, is preferably retained in the soil sampling device to minimize contamination of the soil sample. Furthermore, the previous requirements of manual dexterity are completely eliminated, thereby reducing the sampling time. The soil sampling device also is capable of collecting a plurality of separate samples with the same device to avoid having to use additional sampling devices or make additional trips to a sampling site once the level of analytes therein is known. These and other objects, advantages, purposes, and features of the invention will become more apparent from the study of the following description taken in conjunction with the drawings.

BRIEF DESCRIPTION OF THE DRAWINGS

FIG. 1 is an exploded perspective view of a soil sampling device of the present invention;

FIG. 2A is a cross-sectional view of the soil sampling device of FIG. 1 taken along line II—II;

FIG. 3 is an outside plan view of the cap of the soil sampling device of FIG. 1;

FIG. 4 is an inside plan view of the cap of FIG. 3;

FIG. 9 is a cross-sectional view similar to that of FIG. 8 of another alternate embodiment of the present invention;

FIG. 10A is a cross-sectional view similar to that of FIG. 8 of another alternate embodiment of the present invention;

FIG. 10C is a plan view of another alternative embodiment of the device of FIG. 10A;

FIG. 11B is a cross-sectional view similar to that of FIG. 8 of an alternate embodiment of the device of FIG. 11A;

FIG. 12 is a cross-sectional view similar to that of FIG. 8 of another alternate embodiment of the present invention; and FIG. 13 is a cross-sectional view of the soil sampling device of FIG. 12, taken along line XIII—XIII in FIG. 12.

DESCRIPTION OF THE PREFERRED EMBODIMENTS

Figure 2B:
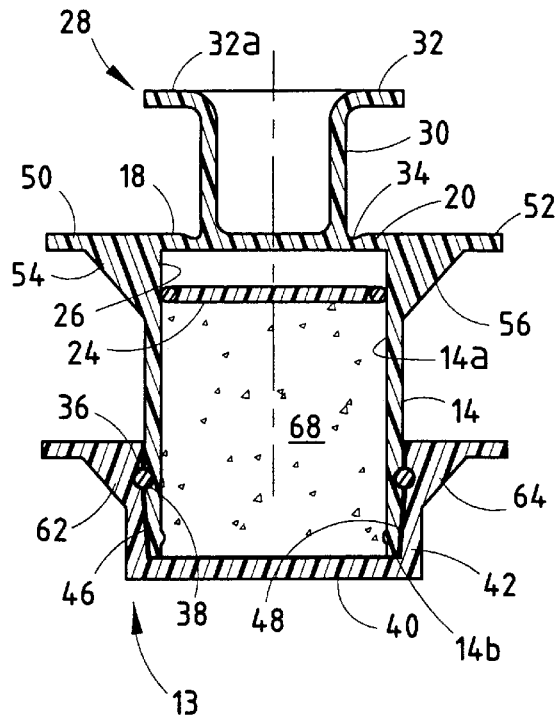
FIG. 2B is a similar view to FIG. 2A with the cap mounted to the body of the soil sampling device.

Referring to FIG. 1, the numeral 10 generally designates a soil sampling device of the present invention. Soil sampling device 10 includes a cylindrical body 12 and a cap 13. Body 12 preferably comprises a plastic material, such as a polymer. More preferably, body 12 comprises a reinforced polymer, such as a glass reinforced polyphthalamide (PPA) and, most preferably, a AMODEL® A-1145 HSPPA Resin, which is available from Amoco Polymers Inc. of Alpharetta, Georgia. As will be more fully described below, soil sampling device 10 is formed or arranged so that when a soil sample is taken, gasses and other particles which may be present in the soil will remain generally undisturbed during the soil sampling process so that an accurate analysis may be performed in a laboratory located either on or off the soil sampling site location.

Cylindrical body 12 includes a cylindrical wall 14 which defines an open end 16 of body 12 on one end and which is closed on the other end 18 by an end wall 20. Open end 16 defines a mouth of sampling device 10 for inserting into soil so that a soil sample can be collected in body 12 of soil sampling device 10. Cylindrical wall 14 extends between end wall 20 and open end 16 along a longitudinal axis 22 of body 12 (FIG. 2A).

Referring to FIG. 2A, a piston 24 is positioned in cylindrical body 12. Piston 24 is held in a chamber 68 defined in body 12 by friction. As best seen in FIG. 2A, piston 24 comprises a dish-shape body having an outer peripheral portion 26 which frictionally engages inner surface 14a of cylindrical wall 14. As will be more fully described below, piston 24 may include one or more seals for frictionally engaging inner surface 14a of cylindrical wall 14. Piston 24 is preferably positioned toward end wall 20 and spaced from open end 16 of cylindrical wall 14. However, it should be understood, that piston 24 may positioned adjacent open end 16 of cylindrical wall 14 before insertion of the soil sampling device into the soil whereby the piston 24 moves along longitudinal axis 22 towards closed end 20 during the collection of a soil sample.

Extending from end wall 20 of body 12 is a projecting member 28. In the illustrated embodiment, projecting member 28 comprises a flanged cylindrical body having a cylindrical wall 30 which is spaced inwardly of cylindrical wall 14 of cylindrical body 12 and which includes an outwardly extending flange 32 to define a contact surface 32a, as will be more 30 fully described below. It should be understood, however, that projecting member 28 may comprise a solid flanged cylindrical body. Preferably, projecting member 28 is integrally molded with end wall 20 to form a unitary soil sampling device. As best seen in FIG. 2A, end wall 20 includes an annular groove 34, which extends around projecting member 28. Annular groove 34 forms a reduced cross-section for end wall 20 and further provides for increased stress concentration factors at the juncture or interface between projecting member 28 and end wall 20. By reducing the cross-section of end wall 20 and increasing the stress concentration factors, annular groove 34 forms a frangible section, which will be more fully explained below.

Again referring to FIG. 2A, cylindrical wall 14 of body 12 includes an annular groove 36 adjacent open end 16 in which a seal 38 is positioned for frictionally engaging cap 13 on open end 16. Cap 13 includes a base or end wall 40 and an annular wall 42 which projects from base 40 for extending over the end portion of cylindrical wall 14 at open end 16. Optionally, inner surface 42a of annular wall 42 of cap 13 includes an annular groove 44 which corresponds and is generally aligned with annular groove 38 of cylindrical wall 14 when cap 13 is placed on cylindrical wall 14. In this manner, when cap 13 is mounted to open end 16 of cylindrical body 12, seal 38 will seat in annular groove 44 and frictionally hold cap 13 on cylindrical wall 14.

Figure 5:
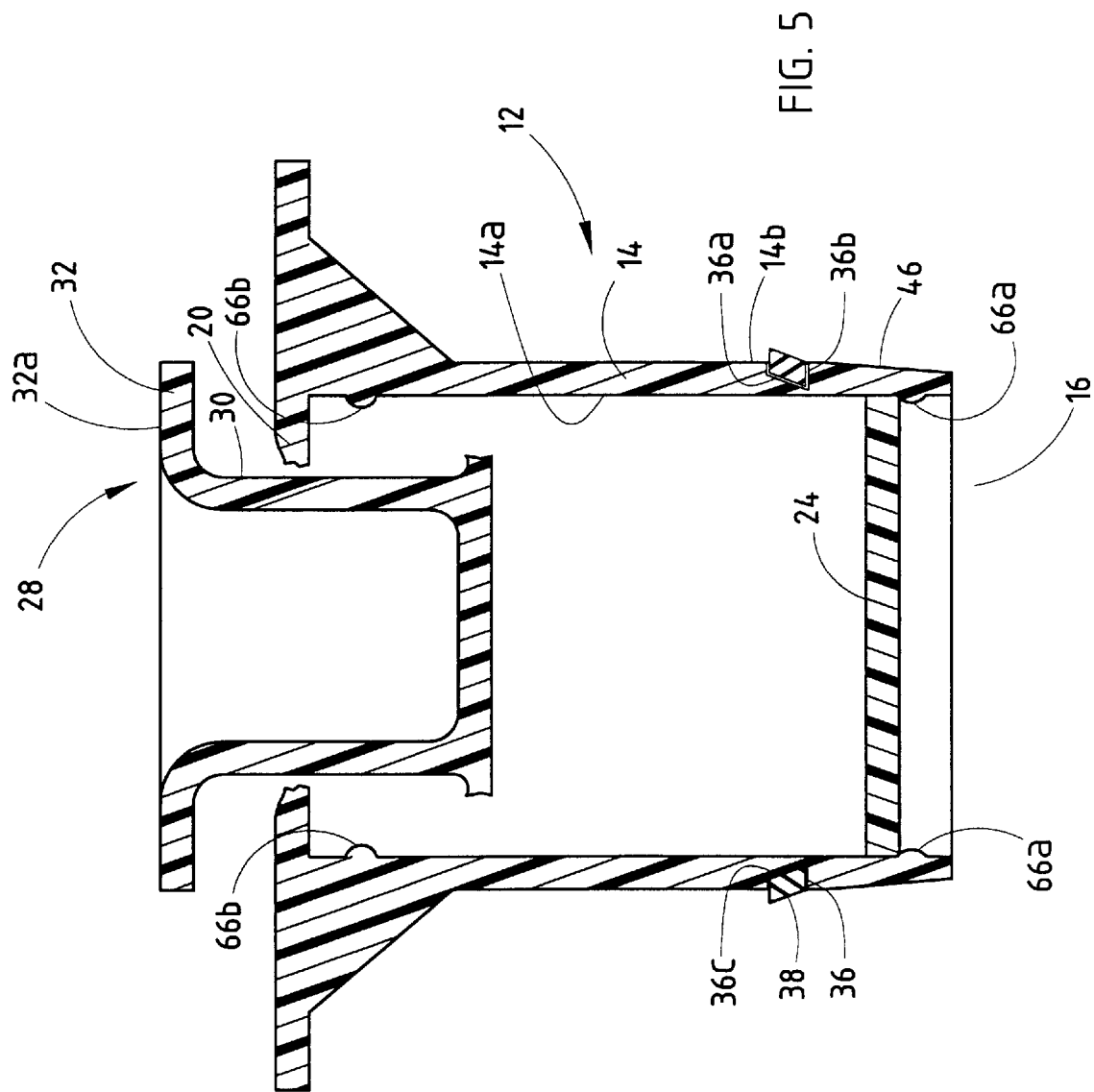
FIG. 5 is an enlarged cross-sectional view similar to FIG. 2A.

Referring to FIGS. 2A and 5, cylindrical wall 14 of body 12 preferably further includes a tapered end portion 46 to ease insertion of body 12 into soil. Furthermore, cap 13 optionally includes a tapered surface 48 on inner surface 42a of annular wall 42 which guides tapered surface 46 of cylindrical wall 14 inwardly when cap 13 is placed on to cylindrical wall 14 at open end 16. In this manner, tapered surface 48 provides further frictional engagement of cap 13 with cylindrical wall 14 of body 12. In addition, referring to FIG. 2B, distal end 14B of cylindrical wall 14 of body 12 contacts or bears against base 40 to thereby eliminate head space between the soil in body 12 and base 40 of cap 13.

To further ease insertion of body 12 into soil, body 12 optionally includes a pair of outwardly extending flanges 50 and 52 which respectively define pressing surfaces 50a and 52a. As best seen in FIG. 2, projecting arms 50 and 52 are integrally molded with body 12 and are positioned near or at closed end 18 of body 12 and are generally flush with end wall 20 of body 12. Optionally, each projecting arm 50, 52 is reinforced by a respective gusset 54 and 56, which likewise may be integrally molded with body 12. In a similar manner, cap 13 may include outwardly projecting arms 58 and 60 which respectively define pressing surfaces 58a and 60a to ease mounting or securement of cap 13 onto body 12 and ease the subsequent removal of cap 13 from body 12. Furthermore, arms 58 and 60 may be reinforced by gusset 62 and 64.

Referring again to FIG. 5, in preferred form, seal 38 comprises a strip seal with a generally rectangular cross-section. Additionally, groove 36 preferably comprises a trapezoidal or similar shaped groove which includes a base wall portion 36a which is angled with respect to the outer surface 14b of cylindrical wall 14. In this manner, when seal 38 is positioned in groove 36, seal 38 is substantially recessed within groove 36 at the bounding side wall 36b of groove 36, which is closer to open end 16, and projects outwardly from groove 36 at bounding side wall 36c of groove 36, which is spaced further from open end 16, for engagement with end cap 13. In this manner, when body 12 is inserted into soil, seal 38 will be compressed against bounding side wall 36c and will remain essentially in place in groove 36, which is particularly suitable for clay soil sampling. In clay soil sampling, the soil tends to pull or twist seals which project outwardly over the full width of the groove. Furthermore, inner surface 14a of cylindrical wall 14 preferably includes one or more retaining ribs 66a which retain piston 24 in body 12. Optionally, projecting rib 66a may comprise an annular projecting ring which extends around the full perimeter of inner surface 14a of cylindrical wall 14. In this manner, piston 24 is retained and not ejected along with the soil sample when the soil sample is expelled from body 12. In addition, inner surface 14a optionally includes a second retaining rib 66b adjacent end wall 20 for limiting the upper movement of piston 24. Therefore, piston 24 is movable between upper and lower positions in body 12 as defined by ribs 66a and 66b. In this manner, the upper most position of piston 24 may define a fixed volume.

Referring again to FIGS. 1, 3 and 4, soil sampling device 10 may further include a holding device 70, for example a strap or a tie. Holding device 70 provides for additional securement of cap 13 to body 12 after a soil sample has been collected. As best seen in FIG. 1, holding device 70 extends over cap and over projecting member 28 to thereby anchor cap 13 to body 12. In order to prevent holding device 70 from shifting, cap 13 may optionally include channel-shaped grooves or recesses 72 and 74 in projecting arms 58 and 60. Recesses 72 and 74 define guides for holding device 70. Furthermore, projecting flange 32 of projecting member 28 may similarly include slotted openings 76 and 78 to likewise receive holding device 70 to further assure that holding device 70 will remain on body 12 and cap 13. It should be understood, that holding device 70 may comprise a conventional tie-wrap or a strap with a corresponding buckle. In this manner, cap 13 will remain on body 12 until soil sampling device 10 reaches the laboratory.

From the foregoing, it can be appreciated that an improved method of taking a soil sample is disclosed. First, open end 16 of body 12 is inserted into soil by applying a compressive force to pressing surfaces 50a and 52a. After chamber 68 is filled with soil, body 12 is removed from the soil by pulling on projecting arms 50 and 52. Once removed from the soil, cap 13 is pressed onto cylindrical wall 14 at open end 16 of body 12 to thereby seal the soil sample in chamber 68. Optionally, holding device 70 may be wrapped around cap 13 and body 12 to thereby further secure cap 13 onto body 12. Once transported to a laboratory, holding device 70 is removed and cap 13 is pulled off open end 16 of body 12. Preferably, body 12 is oriented in a generally vertical orientation and a force, such as impact force, is applied to contact surface 32a of projecting member 28 with a sufficient magnitude to break the frangible section defined by annular recessed groove 34. Once the frangible section is broken, projecting member 28 is pressed into body 12 to contact piston 24 and push piston 24 to thereby expel the soil sample from chamber 68 of body 12. Preferably, projecting rib 66a retains piston 24 in body 12 to thereby eliminate contamination of the soil. After the soil sample is expelled, the soil sampling device 10 is discarded and can not be reused.

Figure 6:
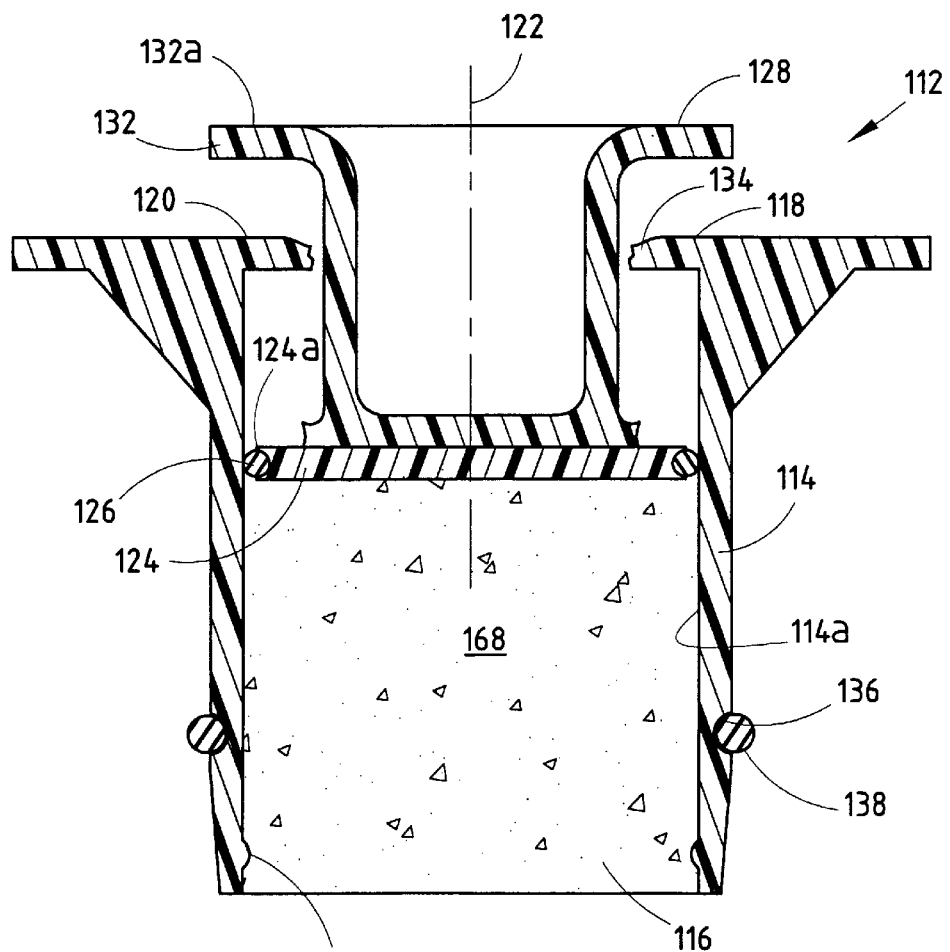
FIG. 6 is a cross-sectional view similar to FIG. 5 illustrating a second embodiment of the soil sampling device of the present invention.

Referring to FIG. 6, a second embodiment of cylindrical body 12 is illustrated. Similar to body 12, cylindrical body 112 includes a cylindrical wall 114 which extends between an open end 116 and a closed end 118. Closed end 118 is defined by an end wall 120. Extending from closed end 120 is a projecting member 128 which is integrally formed with end wall 120. Projecting member 128 has a similar construction to projecting member 28 is integrally molded with end wall 120. End wall 120 includes an annular ring 134 which extends around projecting member 128. Optionally, annular ring 134 comprises a material which has a reduced strength and, therefore, forms a frangible section in end wall 120. Such dissimilar inserts may be achieved by, for example, co-injection molding which is well known in the molding art.

Positioned inside body 112 is a piston 124 which optionally includes at least one seal 126 at its outer peripheral portion 124a for frictionally engaging inner surface 114a of cylindrical wall 114. In the illustrated embodiment, seal 126 comprises an O-ring seal; however, it should be understood that piston 124 may include other suitable seals for frictionally engaging inner surface 114a. Again in a similar manner to the previous embodiment, inner surface 114a of cylindrical wall 114 includes one or more projecting ribs 166 which retain piston 124 in body 112 when the soil sample is ejected from body 112.

As best seen in FIG. 6, end wall 120 optionally has a thinner wall thickness than cylindrical wall 114 to thereby ensure that when a force is applied to projecting member that the end wall 120 will break at recessed groove 134.

In order to retain the cap (which is not shown in this embodiment), cylindrical wall 114 includes a semi-circular groove 136 in which an O-ring seal 138 is positioned for frictionally engaging the cap. Sampling device 110 is more suitable for sampling soils with greater sand content, which unlike clay soil will not tend dislodge seal 138 from groove 136. It should be understood from the foregoing, that body 112 is inserted into the soil in a similar fashion to body 12 of the first embodiment of the soil sampling device. Furthermore, a force is applied to contact surface 132*a* of projecting member 128 to break frangible section 134 so that projecting member 128 may extend into body 112 and push piston 124 along the longitudinal axis 122 of body 112 to thereby expel the soil contained in chamber 168 of body 112.

Figure 7:
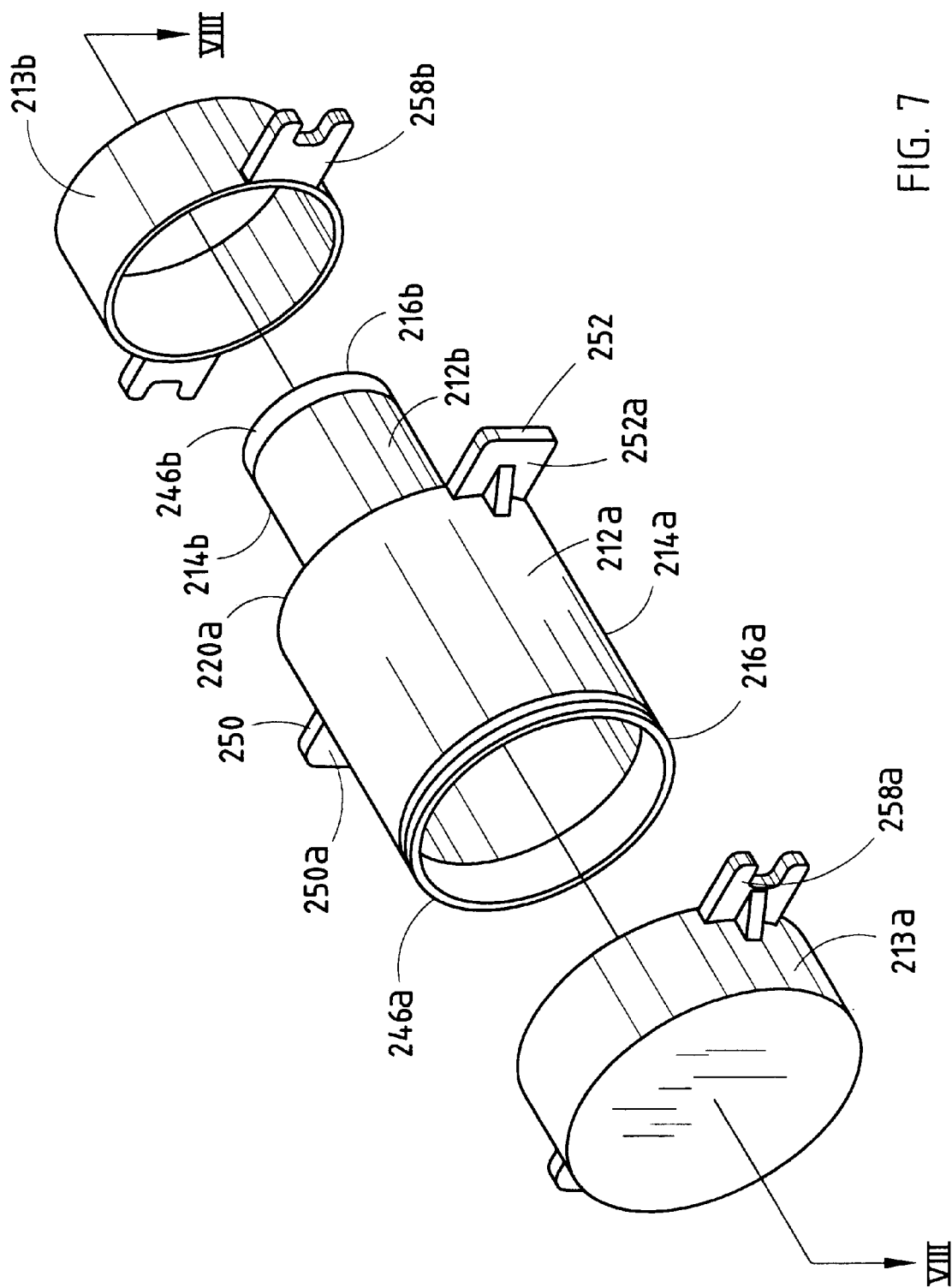
FIG. 7 is an exploded perspective view of an alternate embodiment of the present invention.
Figure 8:
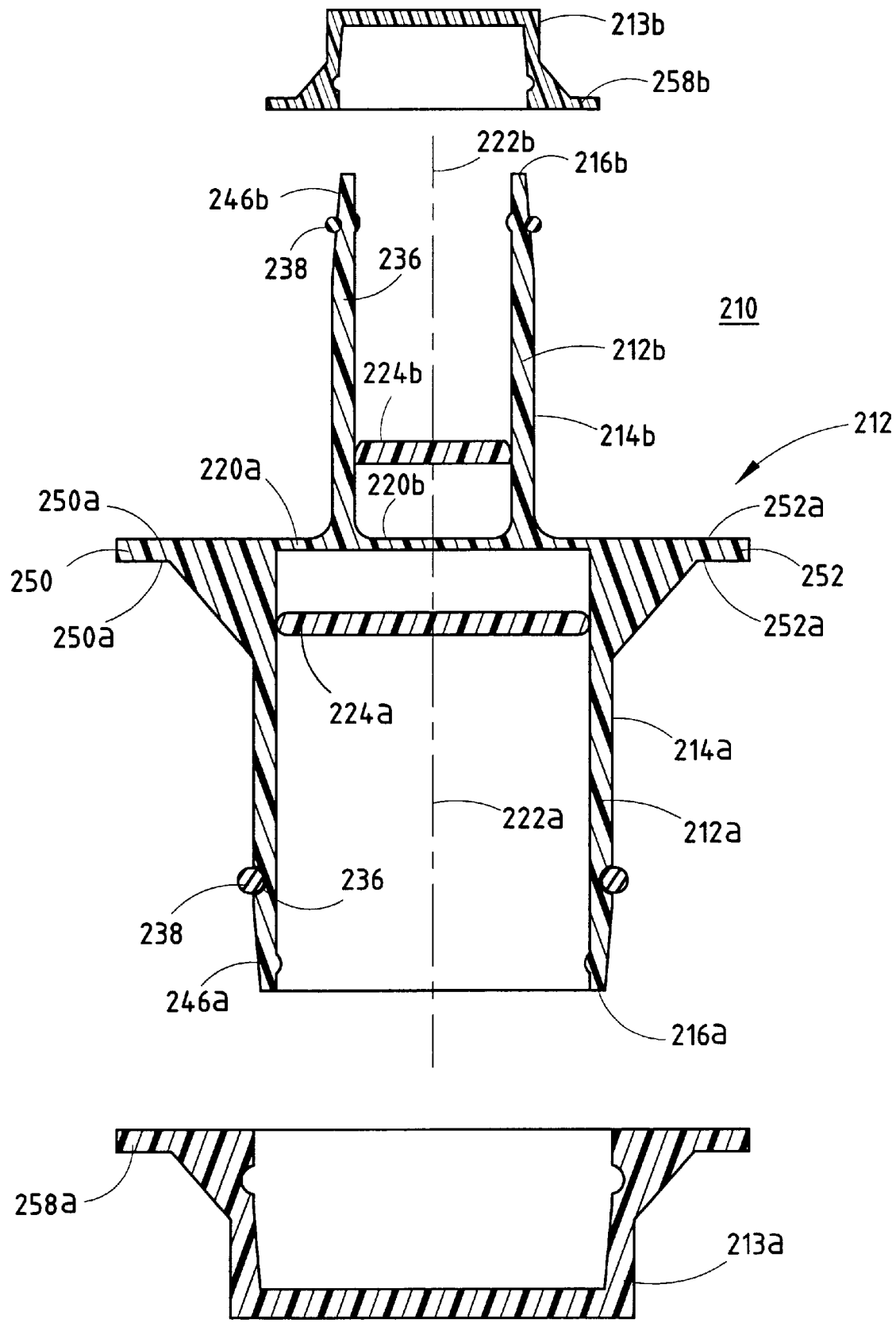
FIG. 8 is a cross-sectional view of the soil sampling device of in FIG. 7 taken along line VIII—VIII in FIG. 7.

Referring to FIGS. 7 and 8, another embodiment of a soil sampling device 210 includes a body 212, which is preferably substantially cylindrical and further includes a first portion 212*a* and a second portion 212*b*. Body 212 preferably comprises a plastic material similar to that of body 12, as discussed above. First portion 212*a* of body 212 preferably includes a substantially cylindrical or barrel-shaped wall 214*a* which has a longitudinal axis 222*a* and defines an open end 216*a* on one end and is closed on the other end by an end wall 220*a*, which further defines a substantially cylindrical chamber in which to collect soil. A piston 224*a*, which may be substantially similar to piston 24 of soil sampling device 10, may be held within first portion 212*a* by friction, as discussed above. Open end 216*a* defines a mouth of first portion 212*a* for inserting into soil so that a soil sample may be collected in first portion 212*a* of soil sampling device 210.

Second portion 212*b* of body 212 further includes a substantially cylindrical or barrel-shaped wall 214*b* which has a longitudinal axis 222*b* and defines an open end 216*b* on one end and is closed on the other end by end wall 220*b*, thereby defining a substantially cylindrical chamber for collecting soil. A piston 224*b* may also be frictionally held within second portion 212*b*, similar to piston 224*a* discussed above. Open end 216*b* further defines a mouth of second portion 212*b* for inserting into soil so that a soil sample can be collected within second portion 212*b* of soil sampling device 210. Second portion 212*b* is positioned substantially co-axially with first portion 212*a* such that closed end 220*b* on second portion 212*b* is interconnected with closed end 220*a* of first portion 212*a*. Although the general shape of body 212, first portion 212*a* and second portion 212*b* are preferably substantially cylindrical, clearly other non-cylindrical shapes, such as rectangular or the like, may be implemented without affecting the scope of the present invention.

Cylindrical walls 214*a* and 214*b* preferably further include a tapered end portions 246*a* and 246*b* to ease insertion of their respective portions 212*a* and 212*b* into the soil. Body 212 may further include a plurality of outwardly extending flanges 250 and 252, which respectively define pressing surfaces 250*a* and 252*a*. The outwardly extending flanges 250 and 252 are preferably integrally molded with body 212 and are positioned substantially adjacent the closed ends of first and second portions 212*a* and 212*b*. The pressing surfaces 250*a* and 252*a* provide a surface on which to exert a force toward the soil to ease insertion of first portion 212*a* or second portion 212*b* into the soil.

First portion 212*a* and second portion 212*b* of body 212 are positioned co-axially adjacent one another, preferably such that end walls 220*a* and 220*b* are unitarily formed with one another, with end wall 220*a* of first portion 212*a* extending radially outward from end wall 220*b* of second portion 212*b*. End wall 220*a* is preferably formed from a reduced cross-sectional area immediately adjacent cylindrical wall 214*a* of first portion 212*a*. By reducing the cross-section of end wall 220*a*, a frangible section is formed which allows end wall 220*a* to break as a force is applied to open end 216*b* of second portion 212*b* in a direction toward first portion 212*a*, thereby allowing second portion 212*b* and end wall 220*b* to function as a plunger in first portion 212*a* to expel the piston 224*a* and soil from therein. End wall 220*b* of second portion 212*b* is likewise formed from a reduced cross-sectional area to allow for end wall 220*b* to be easily broken to ease the expulsion of piston 224*b* and soil from within second portion 212*b*.

Soil sampling device 210 may further include a plurality of end caps 213*a* and 213*b*, for sealing first portion 212*a* and second portion 212*b*, respectively. End caps 213*a* and 213*b* optionally include outwardly projecting arms 258*a* and 258*b*, respectively, to ease mounting or securement of caps 213*a* and 213*b* onto first and second portions 212*a* and 212*b*. As best shown in FIG. 8, cylindrical walls 214*a* and 214*b* of first and second portions 212*a* and 212*b* may include an annular groove 236 adjacent open ends 216*a* and 216*b* in which a seal 238 may be positioned for frictionally engaging end caps 213*a* and 213*b* on open ends 216*a* and 216*b*, which may be similar to soil sampling device 10, discussed above.

Referring to FIG. 9, another alternate embodiment 310 is shown which includes a body 312, which is preferably substantially cylindrical and further includes a first portion 312*a*, which has a longitudinal axis 322*a* and may include a piston 324*a*, and a second portion 312*b*, which has a longitudinal axis 322*b* and may include a piston 324*b*, similar to portions 212*a* and 212*b* discussed above. First and second portions 312*a* and 312*b* are oriented such that their axes 322*a* and 322*b* are substantially co-linear. First portion 312*a* is interconnected to second portion 312*b* by a connecting rod or member 312*c* which is secured to closed ends 320*a* and 320*b* of first and second portions 312*a* and 312*b*, respectively. Member 312*c* may further include a set of wings or tabs 312*d* which extend radially outward from member 312*c*. Wings 312*d* provide a pressing surface to apply a force toward either first or second portion 312*a* and 312*b* to break away the corresponding end wall 320*a* and 320*b* for extrusion of the piston and soil sample contained within the respective portion. As discussed above, end walls 320*a* and 320*b* may include frangible sections around their outer circumferences to ease the insertion of member 312*c* therethrough. Soil sampling device 310 may further include a plurality of end caps 313*a* and 313*b* which seal the respective portions 312*a* and 312*b*. End caps 313*a* and 313*b* may engage their respective portions similar to caps 13 on soil sample 10.

Although soil sampling device 310 is described as having a first and second chamber for collecting separate samples, it is envisioned that the sampling device may include additional chambers or portions, with each chamber having an end wall that is interconnected to the end walls of the other chambers by a common connecting or plunger member. The connecting member may have a plurality of arms extending from a center area toward the end walls of the plurality of portions. Therefore, after the desired number of samples has been collected, a force may be exerted on the center area of the connecting member longitudinally toward a selected chamber to break away the corresponding end wall for extrusion of soil within the selected chamber. This process may then be repeated for the other chambers of the soil sampling device. By including additional chambers on the same sampling device, a user may collect at least two samples for content analysis and an additional sample for dry weight analysis with a single soil sampling device.

Referring to FIG. 10A, another alternate embodiment of a soil sampling device 410 is shown with a first portion 412*a* and a second portion 412b, which are positioned with their corresponding longitudinal axes 422a and 422b being substantially parallel to one another. The end walls 420a and 420b of first and second portion 412a and 412b, respectively, are interconnected by a substantially U-shaped connecting member 412c. Connecting member 412c is secured at each end to end walls 420a and 420b, which may further include frangible sections similar to end walls 20 on soil sample device 10. Connecting member 412c then functions as a plunger for one or both first and second portions 412a and 412b by exerting a force generally parallel to the longitudinal axes 422a and 422b of first and second portions 412a and 412b and toward first and second portions 412a and 412b. This causes the frangible sections on end walls 420a and 420b to break, which allows connecting member 412c to function as a plunger to expel soil from within one or both of first and second portions 412a and 412b. As shown in FIG. 10, soil sampling device 410 may further include one or more end caps 413a and 413b for sealing the soil within first and second portions 412a and 412b, and one or more pistons 424a and 424b for expelling the soil. First and second portions 412a and 412b preferably include tapered open ends and seals for their respective caps, as discussed above in relation to soil sampling device 10.

Figure 10B:
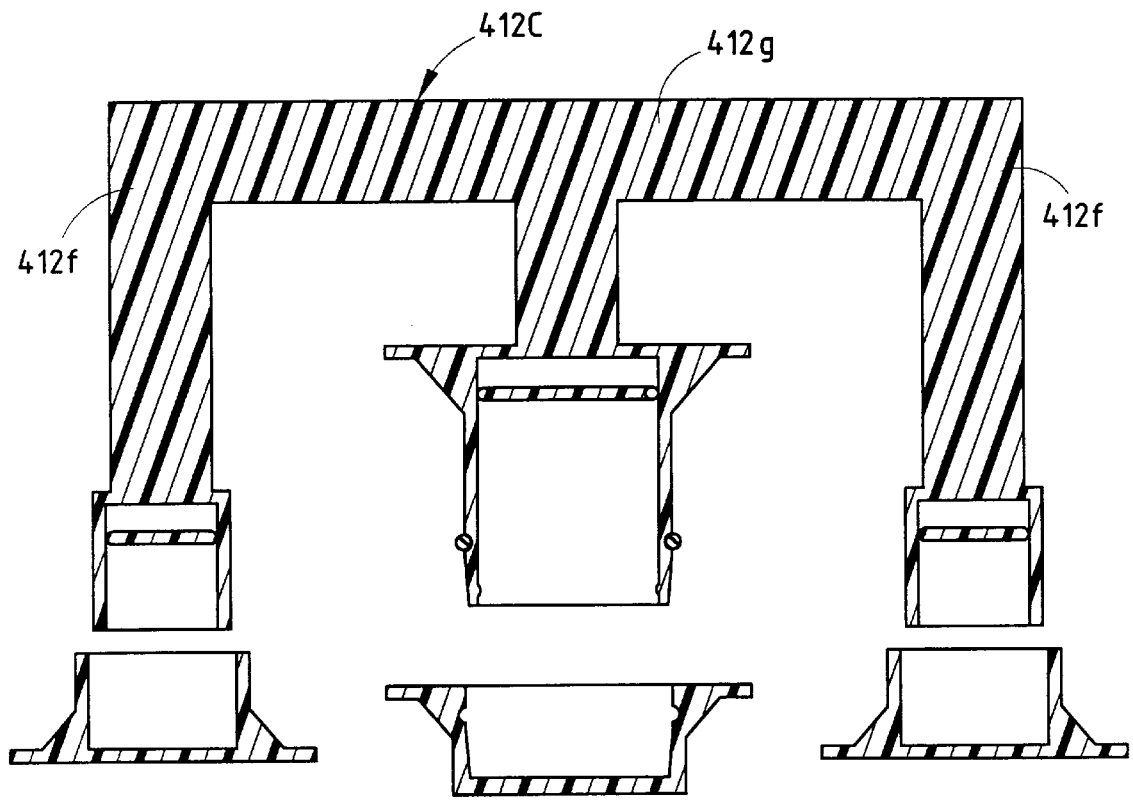
FIG. 10B is a cross-sectional view similar to that of FIG. 8 of an alternate embodiment of the device of FIG. 10A.

As discussed above with respect to sampling device 310, additional chambers may be included on sampling device 410 and interconnected to one another by a connecting member. The additional chambers may be oriented substantially parallel to one another such that the connecting member 412c may include a plurality of arms 412f extending outward from a center portion 412g and downward toward the end wall of each chamber. The longitudinal axes of the chambers may be substantially coplanar with center portion 412g being a substantially straight bar extending over each chamber (FIG. 10B). Alternatively, the parallel chambers may be oriented such that arms 412f extend radially outward from center portion 412g and downward toward each chamber (FIG. 10C).

Figure 11A:
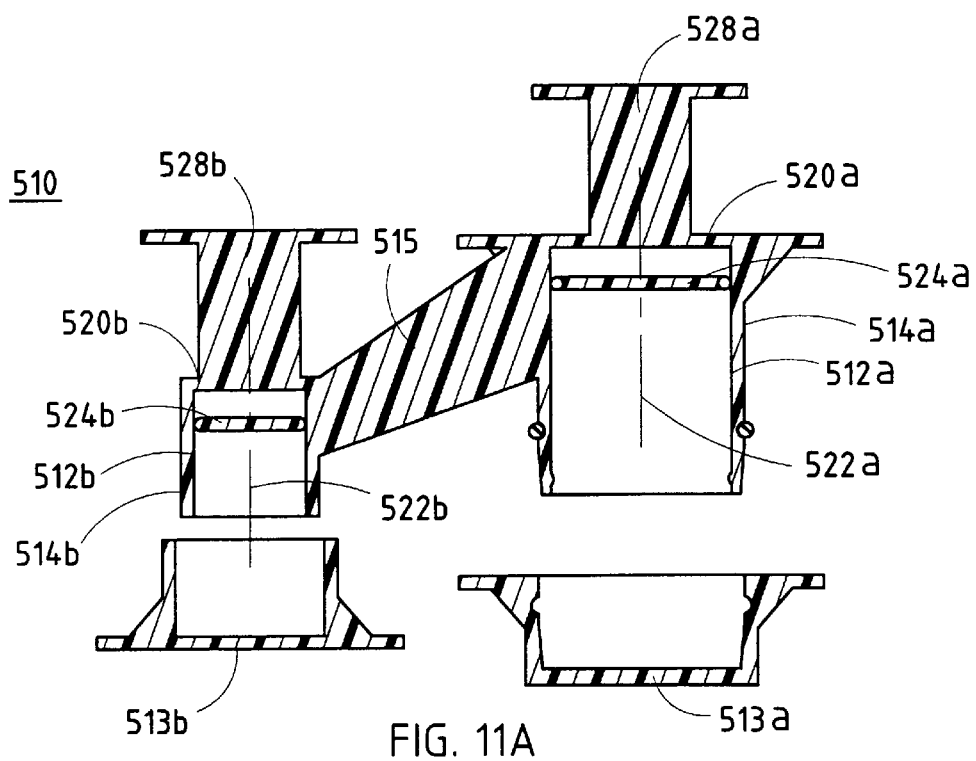
FIG. 11A is a cross-sectional view similar to that of FIG. 8 of another alternate embodiment of the present invention.

Referring to FIG. 11A, there is shown a soil sampling device 510 which is substantially similar to the soil sampling device 410 described above. Soil sampling device 510 includes a first portion 512a which preferably has a cylindrical wall 514a and a second portion 512b which also preferably has a cylindrical wall 514b. Cylindrical walls 514a and 514b are interconnected by a connecting member 515 which secures first and second portions 512a and 512b to one another. First and second portions 512a and 512b are preferably substantially barrel-shaped and may include a piston 524a and 524b within their respective cylindrical walls 514a and 514b. First and second portions 512a and 512b further include end walls 520a and 520b, respectively, upon which a projecting member 528a and 528b is positioned. End walls 520a and 520b preferably include a frangible section along their outer circumferential edges, as discussed above, such that projecting members 528a and 528b may be pushed toward first and second portions 512a and 512b, causing the frangible sections on their end walls 520a and 520b to break. This allows projecting member 528a and 528b to act as plungers in their respective portions, to move pistons 524a and 524b along their respective longitudinal axes 522a and 522b, and thus expel soil from within soil sampling device 510. Additional chambers 512c and corresponding projecting members 528c (FIG. 11B) may also be included which are likewise interconnected by one or more connecting members 515a and 515b. Again, as discussed above with respect to sampling device 310, soil sampling device 510 may further include a plurality of end caps 513a and 513b for sealing a soil sampling within their respective portions 512a and 512b.

Referring now to FIGS. 12 and 13, another alternate embodiment is shown of a soil sampling device 610 which includes a single body 612 and two projecting members 628a and 628b. Body 612 is preferably cylindrical and includes a cylindrical wall 614 and an end wall 620, which together define a substantially cylindrical cavity 617. As best shown in FIG. 13, cylindrical cavity 617 is divided and compartmentalized by an interior wall 614a such that there is a first cavity 617a and a second cavity 617b within cylindrical wall 614. First cavity 617a may be substantially larger than second cavity 617b to provide for varying sample sizes. Furthermore, additional cavities may be provided by including additional dividing walls 614b within body 612. A pair of non-circular pistons 624a and 624b may be frictionally held within the non-cylindrical cavities 617a and 617b. The pistons are formed correspondingly to the semi-circular cross-section of their respective cavities, as best seen in FIG. 13. Projecting members 628a and 628b are connected to end wall 620, which preferably includes frangible sections corresponding to cylindrical wall 614 and dividing wall 614a of cylindrical body 612. This allows either projecting members 628a or 628b or both to be pressed toward cylindrical body 612, thereby breaking one or more of the frangible sections along end wall 620 to allow projecting members 628a and/or 628b to protrude into their respective cavities 617a and 617b to expel pistons 624a and 624b and soil from therein. Soil sampling device 610 may further include tapered edges 646 at its open end 616 and may further include a plurality of outwardly projecting arms 650 and 652 integrally molded with cylindrical body 612 at or near end wall 620, to ease insertion of soil sampling device 610 into the soil. An end cap 613 may also be included to seal soil within one or both of the cavities 617a and 617b. End cap 613 preferably has an outer perimeter wall 613a for engaging cylindrical wall 614 and further has at least one inward projection 613b for engaging dividing wall 614a and any additional dividing walls if applicable, thereby separately sealing each of the cavities within body 612. End cap 613 further may optionally include a plurality of outwardly projecting arms 658 and 660 to ease mounting or securement of cap 613 onto cylindrical body 612, similar to cap 13 discussed above.

Therefore, the multiple chamber embodiments discussed above provide for collecting multiple samples of soil with the same single use soil sampling device. The portions or chambers may also be of different sizes to satisfy various sampling process requirements, so that only a single sampling device is required to collect multiple soil samples. Furthermore, if a dry weight sample is required in addition to the sample to be analyzed, the additional chambers provide for collecting the additional dry weight sample. This avoids the necessity of collecting soil in an additional soil sampling jar and thus further simplifies the sampling process.

While several forms of the invention have been shown and described, other forms will now become apparent to those skilled in the art. For instance, the cylindrical bodies may be formed from a metal material with the frangible section being formed by an insert which is interposed between the projecting member and the end wall of the body of the soil sampling device. Furthermore, the end wall may have an overall reduced wall thickness such that the end wall is thinner than the cylindrical wall, as described previously, but with out a notch or groove thereon. Thus, the end wall comprises the frangible section. In addition, the end wall may have a variable wall thickness to further control the failure mode of the end wall or the frangible sections. The embodiments of the invention shown in the drawings is not intended to limit the scope of the invention which is defined by the claims which follow.

We claim:

1. A soil sampling device comprising:

a body including a plurality of interconnected chambers, each of said chambers having a mouth for inserting into soil for collecting a sample of soil and an end wall opposite said mouth, at least one of said end walls including at least one frangible section thereon;

at least one plunger member interconnected with at least one of said end walls, said at least one plunger member being adapted to break said at least one of said end walls and to extend into at least one of said plurality of chambers when a force is applied to said at least one plunger member in a direction substantially toward said at least one of said end walls, said at least one plunger member thereby providing a plunger for said at least one of said plurality of chambers to expel soil contained therein.

2. The soil sampling device according to claim 1, wherein at least one of said chambers includes a tapered end to ease insertion of said at least one of said chambers into soil.

3. The soil sampling device according to claim 1 further comprising at least one cap for covering at least one of said mouths of said chambers.

4. The soil sampling device of according to claim 3, wherein one of said at least one of said mouths of said chambers and said at least one cap supports a seal for sealing said at least one cap on said at least one of said mouths.

5. The soil sampling device according to claim 1, wherein at least a portion of said at least one of said end walls includes a reduced cross-section, said reduced cross-section forming said at least one frangible section, and being adapted to break when a force is applied to said at least one plunger member.

6. The soil sampling device according to claim 1, wherein said body includes outwardly projecting arms to provide pressing surfaces for pressing at least one of said chambers into soil for collecting a soil sample.

7. The soil sampling device according to claim 1 further including at least one piston movably positioned within at least one of said plurality of chambers, said at least one piston being moved through said at least one of said chambers to expel soil contained therein.

8. The soil sampling device according to claim 1, wherein said plurality of chambers are interconnected by said at least one plunger member, said at least one plunger member being interconnected to said end wall of each of said plurality of chambers.

9. The soil sampling device according to claim 8, wherein said at least one plunger member includes at least one pressing surface upon which said pressure is applied toward said at least one of said plurality of chambers.

10. The soil sampling device according to claim 8 further including at least one piston movably positioned within at least one of said plurality of chambers, said at least one piston being moved through said at least one of said chambers by said at least one plunger member to expel soil contained therein.

11. The soil sampling device according to claim 8, wherein said at least one plunger member is unitarily formed with each of said chambers.

12. The soil sampling device according to claim 8, wherein said body comprises a first chamber and a second chamber, said first chamber having a first longitudinal axis and said second chamber having a second longitudinal axis, wherein said first and second longitudinal axes are co-linear.

13. The soil sampling device according to claim 12, wherein said first and second chambers are interconnected at said end walls, at least a portion of said end wall of said first chamber forming said end wall of said second chamber such that said plunger member comprises said second chamber, said end wall of said first chamber including said at least one frangible section, said at least one frangible section being located radially outward from said end wall of said second chamber such that when a pressure is applied to said second chamber to compress said first end wall, said at least one frangible section breaks and said second chamber enters said first chamber and provides a plunger for said first chamber to expel soil contained therein.

14. The soil sampling device according to claim 12, wherein said end wall of said first chamber includes a first frangible section and said end wall of said second chamber includes a second frangible section, such that when a pressure is applied longitudinally along said plunger member, at least one of said first and second frangible sections breaks and said plunger member provides a plunger for at least one of said first and second chambers to expel soil contained therein.

15. The soil sampling device according to claim 8, wherein said body comprises at least three chambers, said at least one plunger member including at least three arms extending from a center portion of said at least one plunger member to said end walls of said at least three chambers.

16. The soil sampling device according to claim 15, wherein said at least three arms extend radially outward from said center portion, said at least three chambers being oriented substantially co-planar with one another.

17. The soil sampling device according to claim 8, wherein each of said chambers has a longitudinal axis, said longitudinal axes being substantially parallel, said at least one plunger member including a plurality of arms and a center portion, said arms extending from said center portion longitudinally toward said chambers.

18. The soil sampling device according to claim 17, wherein said plurality of chambers comprises a first chamber and a second chamber, said at least one plunger member being substantially U-shaped.

19. The soil sampling device according to claim 17, wherein said plurality of chambers comprises at least three chambers, said at least one plunger member including at least three arms extending from said center portion.

20. The soil sampling device according to claim 17, wherein each of said end walls of said plurality of chambers includes a frangible section such that when a pressure is applied to said at least one plunger member longitudinally toward said plurality of chambers, said plunger member breaks said frangible sections and enters each of said plurality of chambers to simultaneously expel soil contained therein.

21. The soil sampling device according to claim 1, wherein said plurality of chambers are interconnected by a connecting member.

22. The soil sampling device according to claim 21, wherein said body comprises a first chamber and a second chamber, said at least one plunger member comprising a first plunger and a second plunger, said first plunger interconnected with said end wall of said first chamber and said second plunger interconnected with said end wall of said second chamber.

23. The soil sampling device according to claim 22, wherein said first and second chambers are further interconnected by at least one plunger member.

24. The soil sampling device according to claim 21, wherein said body comprises at least three chambers, said at least one plunger member being interconnected with at least one of said end walls of said at least three chambers.

25. The soil sampling device according to claim 1, wherein said body is compartmentalized by at least one dividing wall to form said plurality of chambers, said plurality of chambers being interconnected by at least one of an exterior wall of said body and said at least one dividing wall.

26. The soil sampling device according to claim 25, wherein said at least one dividing wall forms at least a portion of a wall of a first chamber and said at least one dividing wall further forms at least a portion of a wall of a second chamber, a first portion of said exterior wall and said at least one dividing wall define a first mouth of said first chamber and a second portion of said exterior wall and said at least one dividing wall define a second mouth of said second chamber.

27. The soil sampling device according to claim 25, wherein said body includes at least two dividing walls, said body being compartmentalized into at least three chambers.

28. The soil sampling device according to claim 25 further comprising a cap for closing said mouths of said plurality of chambers, said cap having an outer perimeter wall for engaging an outer surface of said exterior wall of said body.

29. The soil sampling device according to claim 28, wherein said cap further includes at least one projecting member for separately sealing at least one of said plurality of chambers.

30. A soil sampling device comprising:
   a body having a first end wall and a first mouth defining a first chamber therebetween and a second end wall and a second mouth defining a second chamber therebetween, said first chamber having a first longitudinal axis and said second chamber having a second longitudinal axis, said first and second chambers being interconnected, and said first end wall including a first frangible section and said second end wall including a second frangible section;
   at least one plunger member interconnected with at least one of said first and second frangible sections, such that when a pressure is applied to said at least one plunger member, said at least one of said first and second frangible sections breaks and said at least one plunger member provides a plunger for at least one of said first and second chambers to expel soil contained therein; and
   a first cap and a second cap for respectively closing said first and second mouths of said first and second chambers.

31. The soil sampling device according to claim 30, wherein said at least one plunger member comprises said second chamber, said first end wall and said second end wall forming a common end wall such that said first and second chambers are interconnected by said common end wall, such that when a compressive force is applied to said second chamber, said first frangible section breaks and permits said second chamber to enter said first chamber to form a plunger.

32. The soil sampling device according to claim 30, wherein said at least one plunger member comprises a first plunger member interconnected to said first end wall and a second plunger member interconnected to said second end wall.

33. The soil sampling device according to claim 32, wherein said first and second plunger members are unitarily formed with said first and second end walls, respectively.

34. The soil sampling device according to claim 32, wherein said first and second plunger members are interconnected.

35. The soil sampling device according to claim 34, wherein said body further includes a third chamber and a third plunger member, said third chamber being interconnected to said first and second chambers by said plunger members.

36. The soil sampling device according to claim 34, wherein said first and second longitudinal axes are substantially co-linear.

37. The soil sampling device according to claim 34, wherein said first and second longitudinal axes are substantially parallel.

38. The soil sampling device according to claim 37, wherein said body further includes a third chamber and a third plunger member.

39. The soil sampling device according to claim 30, wherein said first and second chambers are interconnected by at least one common wall extending longitudinally within said body.

40. The soil sampling device according to claim 39, wherein said body includes a third chamber, said first, second and third chambers being interconnected by one of said at least one common wall and an exterior wall of said body.

41. The soil sampling device according to claim 30, wherein said first and second chambers are interconnected by at least one connecting member extending from an exterior surface of said first chamber to an exterior surface of said second chamber.

42. The soil sampling device according to claim 41, wherein said body includes a third chamber interconnected to at least one of said first and second chambers by said at least one connecting member.

43. The soil sampling device according to claim 30, wherein at least one of said first chamber and said first cap supports a seal for sealing said first cap on said first chamber.

44. The soil sampling device according to claim 30, wherein each of said first and second caps includes outwardly projecting arms to provide pressing surfaces for said respective first and second caps.

45. The soil sampling device according to claim 30, wherein said body includes outwardly projecting arms to provide pressing surfaces for pressing at least one of said first and second chambers into soil for collecting a soil sample.

46. The soil sampling device according to claim 30, wherein said at least one plunger member includes a pressing surface for pressing said at least one plunger member toward said at least one of said first and second chambers to break said at least one frangible section and expel soil contained within said at least one of said first and second chambers.

47. The soil sampling device according to claim 30 further includes at least one piston movably positioned within at least one of said first and second chambers, said piston being moved through said at least one of said first and second chambers by said at least one plunger member to expel soil contained within said at least one of said first and second chambers.

* * * * *